US00PP17683P3

(12) United States Plant Patent
Doyle

(10) Patent No.: US PP17,683 P3
(45) Date of Patent: May 1, 2007

(54) ***GLECHOMA* PLANT NAMED 'DAPPLED LIGHT'**

(50) Latin Name: *Glechoma hederacea*
Varietal Denomination: Dappled Light

(76) Inventor: Alice J. Doyle, 78185 Rat Creek Rd., Cottage Grove, OR (US) 97424

( * ) Notice: Subject to any disclaimer, the term of this patent is extended or adjusted under 35 U.S.C. 154(b) by 45 days.

(21) Appl. No.: 11/110,387

(22) Filed: Apr. 20, 2005

(65) Prior Publication Data

US 2006/0242743 P1 Oct. 26, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Donald D. Jeffery

(57) ABSTRACT

A new and distinct *Glechoma* plant named 'Dappled Light,' particularly characterized by its unique variegation. The main or ground cover of the upper surface of mature leaves is a medium green, with the reticulated pattern and veining being a very pale green. The leaf stems, when exposed to sunlight, have a pinkish-purple color, which pleasantly contrasts with the variegated leaves. The new cultivar has relatively long internodal spacing thereby producing a fuller and more open plant.

1 Drawing Sheet

Botanical designation: *Glechoma hederacea.*
Variety denomination: 'Dappled Light'.

BACKGROUND OF THE INVENTION

The present invention relates to a new and distinct cultivar of *Glechoma* plant, botanically known as *Glechoma hederacea,* and referred to by the cultivar name, 'Dappled Light.'

*Glechoma* is a genus of approximately ten species of creeping decumbent plants. The species *Glechoma hederacea* is a perennial, having pairs of round, scalloped, bright green leaves and occasional small, trumpet-shaped, blue flowers. The species is commonly known by numerous other names, including Creeping Charley, Gill-on-the-Ground or Gill-Over-the-Ground, Runaway Robin, Ground Ivy, Field Balm, and Alehoof. The normal use of the species is as small-scale ground cover or in hanging baskets. It can be a serious lawn and garden weed.

BRIEF SUMMARY OF THE INVENTION

The new cultivar was discovered by the inventor in May 2001 as a naturally occurring branch mutation of a plant of *Glechoma hederacea,* growing among plants of that species in a greenhouse in Cottage Grove, Oreg. The parent is unpatented and has no varietal denomination. The mutation was immediately recognized by the very different color and variegation of its leaves.

The first act of asexual propagation of the new cultivar was accomplished when tip cuttings were taken from the branch mutation in May 2001 by the inventor in a controlled environment in Cottage Grove, Oreg. Horticultural examination of plants of successive generations has shown that the unique combination of characteristics of 'Dappled Light' are firmly fixed and are retained through successive generations of asexual reproduction.

The following traits have been repeatedly observed and have been determined to be basic characteristics of the new cultivar which, in combination, distinguish the new cultivar as being new and distinct.

1. The leaf variegation is uniquely different, yet stable and uniform.
2. The variegation comprises fine, dappled, light green spots throughout the leaf surface, with the veining being the same light green. The dappling is fairly consistent from leaf to leaf.
3. The leaves are uniformly placed on the branches, thereby enhancing the visual impact and beauty of the plant.
4. The leaf stems are pinkish-purple when exposed to sunlight, providing a striking contrast with the dappled green leaves.
5. The new cultivar can be used as ground cover or as a trailing accent in a mixed combination of plants.
6. The new cultivar is a moderate but vigorous grower, and is easy to propagate.
7. Although plants of 'Dappled Light' may occasionally show a few blooms in late summer when grown in Cottage Grove, Oreg., the flowers are considered inconsequential.

Of the commercial cultivars known to the inventor, the most similar in comparison to 'Dappled Light' is the parent from which it mutated. The leaves of the parent have distinct, irregular blotches of green and white, with nonuniform white edging. The leaves of the new cultivar have a distinctly different medium green background and a light green, reticulated pattern and veins.

BRIEF DESCRIPTION OF THE DRAWINGS

The accompanying sheet of photographs shows the characteristics of the new cultivar, with the colors being as nearly true as possible with illustrations of this type.

The photo at the bottom shows a plant ready for sale in a pot container.

The photos at the top comprise close-up views of the new cultivar, showing in more detail the unique variegation of the leaves and the pinkish-purple leaf stems.

DETAILED BOTANICAL DESCRIPTION

The new cultivar has not been observed under all possible environmental conditions. The phenotype may vary significantly with variations in environment, such as temperature, light intensity, and day length without, however, any variance in genotype. The following observations, measurements, and comparisons describe plants grown in Bonsall, Calif., in sun to partial shade, day temperatures of 18.3 degrees C. to 23.8 degrees C. and night temperatures of up to 12.8 degrees C. Normal commercial growing conditions were used.

In the following description, color references are made to The Royal Horticultural Society Colour Chart. The values are based on plant material grown in Bonsall, Calif., and the values were taken in early April.

Parentage: 'Dappled Light' is a naturally occurring branch mutation taken from an unpatented and unnamed plant of the species.

Botanical classification: *Glechoma hederacea.*

Roots: Roots are white and fine; roots are initiated in 12 days in summer at 20 degrees C. and 20 days in winter at the same temperature; a rooted cutting or liner is produced in four weeks in summer at 20 degrees C., and five weeks in winter at the same temperature.

Habit: 'Dappled Light' is a low, creeping/vining perennial, hardy to approximately 12 degrees C. (hardiness zones 5–11). Plant height is approximately 10 cm., and the area of spread of a typical specimen plant is approximately 48 cm. However, growth is indeterminate. It is graceful and delicately trailing. Growth rate is moderate due to variegation of leaves, but plant vigor is very good.

Pinching is recommended two weeks after planting the liner. There is strong apical dominance, and plants can also be cut back to promote the development of the latest axillary shoots, which results in a fuller plant.

No basal shoots were observed, but the creeping stems develop adventitious roots at the nodes, and will root if in contact with the soil.

Lateral shoots: The number of lateral shoots is highly variable, but averages six–seven per plant. Lateral branch length varies as well, averaging approximately 24 cm. Diameter of the stems is only 0.15 cm, and the slender stems are squarish, covered in short, scattered, white hairs (pubescent). Internodes are relatively long — 6.2 cm — and the long internode results in a loose, open plant habit. The lateral branches have approximately the same range of color as the stems.

Stems: Stems are initially upright, but stem strength is only fair, and stems then fall over and grow horizontally along the soil. The surface texture is pubescent. the ground color of stems is light green (RHS 145D), but if exposed to sunlight, they develop a greyed, rose-violet tint (RHS 185D). This rose tint provides a nice decorative effect contrasted with the variegated leaves.

There are latent axillary shoots, two per node, which develop into lateral shoots if the shoot tip is pinched. Although the stems creep along the soil surface, the leaves tend to curve on their petioles to face upward toward the light.

Leaves: Leaves are opposite and simple. The numbers of leaves per branch varies with its length, but an average stem has approximately 14 visible leaves. The leaf shape is reniform to orbicular (see photos). The leaf tip is rounded, and the leaf base i3n cordate. Leaf margins are regularly crenate/scalloped. Leaf length averages 4.2 cm; leaf width averages 4.6 cm. The texture of the leaves is slightly sandpapery on both sides due to the short, scattered hairs, more of which are on the lower side, especially along the veins. The leaf venation pattern is palmate toward the base, becoming reticulate toward the margins.

Young leaves are RHS 146C on the upper side, and are RHS 146D on their lower side with slight variegation showing on the upper surface. As leaves expand and mature, the dappled variegation develops (see photos). On the upper side, the ground color of the mature leaf is medium green, RHS 146A, with an overall random reticulated or dappled pattern of very pale green, RHS 145D. Leaf color of mature leaves on their underside is RHS 147C and D. Vein color of mature leaves is RHS 145D on the upper side, and RHS 194C on the lower side.

Leaf petioles: Leaf petiole length is highly variable, and depends on the position of the leaf on the stem. (Older, mature basal leaves have longer petioles than young leaves at shoot tips.) An average leaf petiole is approximately 7.5 cm. Petiole diameter is only 0.1 cm. Petioles are slightly rough and pubescent. Petiole color on the upper side is generally RHS 195C, but often it is tinged with grey-pink (RHS 182C) if exposed to the sun. Petiole color on the lower side is RHS 195C.

Other foliage characteristics: No stipules, tendrils, thorns, or spines were observed. The broadly scalloped, kidney-shaped leaves are decorative, with a fine, reticulate, pale green variegation. The long petioles tend to have an upright aspect so that leaf blades are held nearly horizontally, even on creeping steps.

Flowers or buds: The plant shown in the photos and from which the above description was made did not express budding or flowering. However, plants of the new cultivar do flower occasionally, usually between March and August, and when doing so the blooms are identical to other plants of the species. The flowers are light violet blue in color, trumpet shaped, and about ⅜ to 5/16 inches long. The flower characteristics are inconsequential.

Reproductive organs: When the plant does flower, each bloom has one two-lobed pistil approximately 7 mm, long, with a purple stigma and white style; there are four white stamens, each approximately 7 mm long.

Fruit: None observed.

Fragrance: None observed.

I claim:

1. A new and distinct *Glechoma* plant named 'Dappled Light,' as described and illustrated.

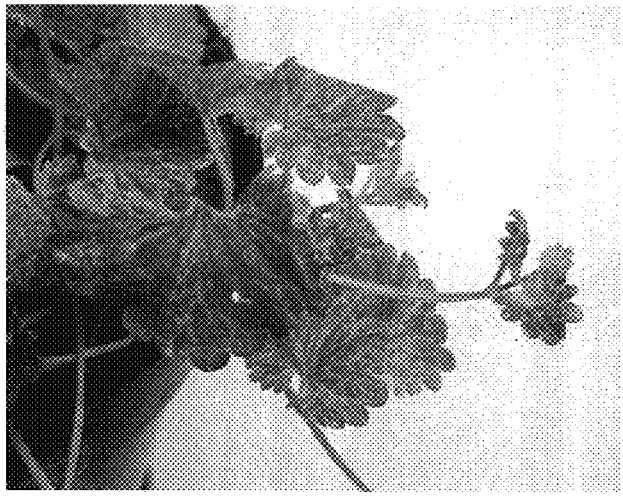
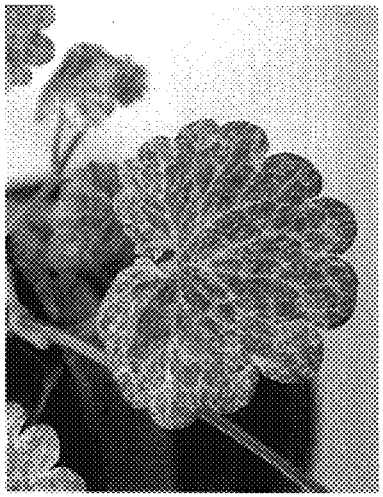
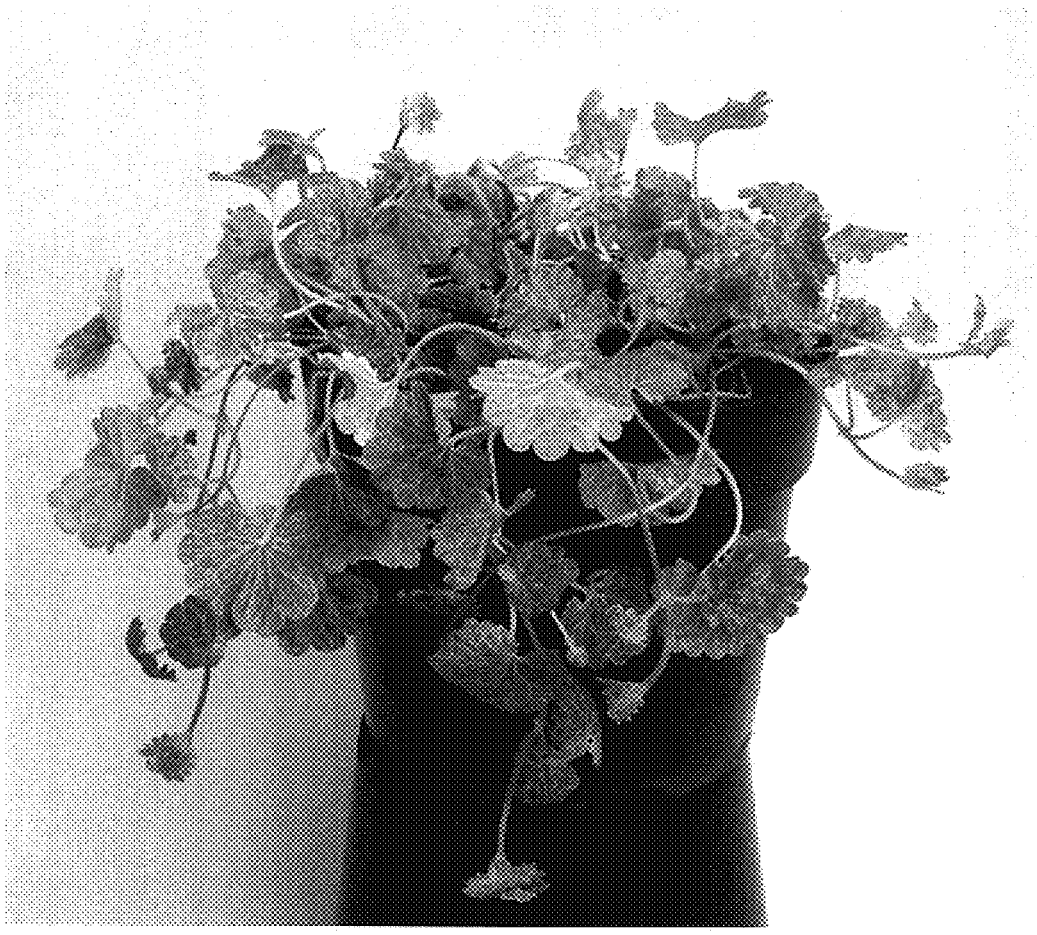

* * * * *